US006578424B1

(12) United States Patent
Ziola et al.

(10) Patent No.: US 6,578,424 B1
(45) Date of Patent: Jun. 17, 2003

(54) HAND-HELD VARIABLE ANGLE MEMBRANE (VAM) ULTRASONIC SCANNING HEAD FOR THE NONINVASIVE DETECTION OF CORROSION, MIC AND FOREIGN OBJECTS IN PIPES

(75) Inventors: Steven M. Ziola, Littleton, CO (US); Michael R. Gorman, Englewood, CO (US); William J. Miller, Aurora, CO (US)

(73) Assignee: Digital Wave Corporation, Englewood, CO (US)

( * ) Notice: Subject to any disclaimer, the term of this patent is extended or adjusted under 35 U.S.C. 154(b) by 0 days.

(21) Appl. No.: 09/671,405

(22) Filed: Sep. 27, 2000

(51) Int. Cl.[7] .............................................. G01N 29/00
(52) U.S. Cl. ........................................ 73/632; 73/644
(58) Field of Search .................... 73/632, 633, 640, 73/641, 644, 622, 634, 637, 638, 639

(56) References Cited

U.S. PATENT DOCUMENTS 4,407,293 A * 10/1983 Suarez, Jr. et al. ......... 128/660
5,426,980 A * 6/1995 Smith ........................... 73/644
5,585,565 A * 12/1996 Glascock et al. ............. 73/644

* cited by examiner

Primary Examiner—Richard A. Moller
(74) Attorney, Agent, or Firm—Jonathan Anan Quine; Quine Intellectual Property Law Group, P.C.

(57) ABSTRACT

A hand-held Variable Angle Membrane (VAM) ultrasonic scanning head consisting of transmitting and receiving transducers is used to excite guided waves to detect corrosion, MIC and foreign objects in containers such as pipes. The scanning head includes transducers mounted on a fluid filled housing sealed by a membrane. This system couples ultrasound from the transducer to the pipe wall. The transducer housings are mounted in a rigid frame that holds the ultrasonic transducer housings a specific distance apart and allows each transducer housing to rotate about a pivot point. The membrane deforms to the pipe diameter to be scanned. The scanning head is adjusted to perform inspections in various container diameters and thicknesses. Once adjusted for diameter and thickness, the operator places the scanning head on the pipe and couples the rubber membranes to the pipe with a small amount of couplant. Separate electronics excite the transmitting transducer, and then condition the signal from the receiving transducer for analysis.

29 Claims, 2 Drawing Sheets

HAND-HELD VARIABLE ANGLE MEMBRANE (VAM) ULTRASONIC SCANNING HEAD FOR THE NONINVASIVE DETECTION OF CORROSION, MIC AND FOREIGN OBJECTS IN PIPES

COPYRIGHT NOTICE

Pursuant to 37 C.F.R. 1.71 (e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF INVENTION

This invention relates to noninvasive testing of the internal conditions of fluid-filled containers such as pipes, especially to a novel ultrasonic hand-held variable angle membrane (VAM) scanning head for such testing purposes.

BACKGROUND OF THE INVENTION

Detecting inner wall corrosion in pipes, cylinders, tanks, pressure vessels, and other containers has been a longstanding concern in many industries. MIC (microbiologically influenced corrosion) in water systems is of particular concern. The microbes live in water everywhere and are difficult to kill. Corrosion pitting, slimy fluid and rusty nodules are often the products of MIC. Corrosion and foreign objects in pipes and other containers cause wall thinning and reduction of flow areas that are detrimental to the structural performance of the pipes, and can sometimes lead to disastrous consequences. The chemical, petroleum, water utility and power industries have been battling MIC for many years.

The use of ultrasonic waves for the inspection of pipes uses transducers coupled to the pipe at a correct angle for excitation and detection of various wave modes used for MIC detection. Coupling of the transducers is complicated by the curvature of the pipe or other container under inspection.

Typical approaches in ultrasound detection use solid Lucite® or plastic wedges (or shoes) or fluid filled rubber wheels to couple the ultrasound into the pipe. When using plastic shoes, the shoes are machined so that the transducers are positioned at a correct angle to the pipe surface to create the guided wave mode of interest, while the contact area of the shoes are machined to fit the curvature of the pipe. While this approach works, it requires manufacture of a large number of shoes to cover the various diameters of pipe and other containers in use, since each pipe or other container diameter requires a different radius shoe.

Also, the user either needs transducers for each set of shoes, or has to move the transducers to a new set of shoes if a different pipe size is to be inspected. This takes time, and can result in damaged transducers due to the large amount of handling involved.

The wheel method places the ultrasonic transducer inside a fluid filled wheel. The wheel is then rolled over the surface to be inspected. The fluid couples the sound from the transducer to the rubber wheel and the rubber wheel couples the sound into the part under inspection (e.g., container wall, etc.). For angles other than normal to the part surface (guided wave ultrasonics requires angling the sensor to excite the correct wave modes), angular positioning of the transducer becomes difficult. Also, depending on the size of the transducers, the wheels can be large and difficult to handle.

The present invention overcomes the problems of the prior art by providing compact adjustable hand-held ultrasonic scanning heads for pipes and other containers. These and other features of the invention will be clear upon review of the following.

SUMMARY OF THE INVENTION

As noted, the present application provides compact handheld ultrasonic scanning heads for pipes and other containers. These hand held scanning heads are on the order of a few inches in length, width and height. For example, in one embodiment, the external dimensions of an exemplar scanning head is about 6 inches long by about 3 inches wide by about 3 inches high. The transducers are mounted on pivot points in a rigid frame, allowing for control of angular positioning of the transducer sensors for guided wave excitation and detection. Coupling is performed through a rubber membrane, which conforms to various diameters of pipe. This design eliminates positioning errors that occur with a fluid filled wheel, and does not require a new set of shoes for each pipe diameter. The compact size allows the head to be used in confined areas encountered in inspections.

Accordingly, a hand-held variable angle membrane (VAM) MIC ultrasonic scanning head is described for fast and repeatable coupling of ultrasound into pipes, tanks, plates, pressure vessels, etc., for the detection of corrosion, MIC and foreign obstructions.

In the methods of the invention, an ultrasonic transmitting transducer is used to couple ultrasound into the pipe or other container to excite guided waves, which propagate away from the transducer along the pipe wall. A receiving transducer is used to detect ultrasound excited by the transmitting transducer after it has traveled along the pipe wall.

The head design incorporates a flexible polymer (e.g., rubber) membrane to contact the pipe surface. The membrane conforms to the pipe diameter, providing a stable, repeatable ultrasonic coupling of the ultrasound into the pipe over any diameter. The ultrasound from the transducer is coupled to the membrane through a fluid filled cavity. The transducer is attached and sealed to one end of a hollow housing, so that only the face of the transducer contacts the coupling fluid. This eliminates having to place the entire transducer in the coupling fluid as is done in a wheel-based method. The rubber membrane is attached and sealed to the other end of the housing. The cavity between the transducer face and the rubber membrane is filled with fluid. The membrane is specially shaped to extend outward beyond the base of the housing so that it can deform to the pipe surface in a fluid-like manner ensuring good coupling to the pipe. Sound is coupled from the transducer to the membrane through the fluid.

Fluid filled housings are mounted on pivot pins in a rigid frame. The frame ensures that the transducers are held a specific selected distance apart, and the pivot pins allow each housing to be rotated a known angle for ultrasound injection into the pipe wall. The frame also allows the operator to easily hold and position the transducers on the pipe to be inspected. The rubber membranes are coupled to the pipe with a suitable couplant, such as a small amount of water or ultrasonic gel.

By incorporating the membrane, any diameter of pipe can be scanned, since the membrane deforms to the pipe diameter. The ability to rotate each housing allows the user to adjust the angle of the ultrasonic transducers for each pipe diameter and thickness for excitation of the correct guided wave mode for the inspection of corrosion and obstructions.

Quick connect electrical connections between the transducers and the system electronics allow for easy replacement or changing of scanning heads.

Further features and advantages of the invention will become apparent from a consideration of the drawings, detailed description and claims.

DETAILED DISCUSSION OF THE INVENTION

Figure 1:
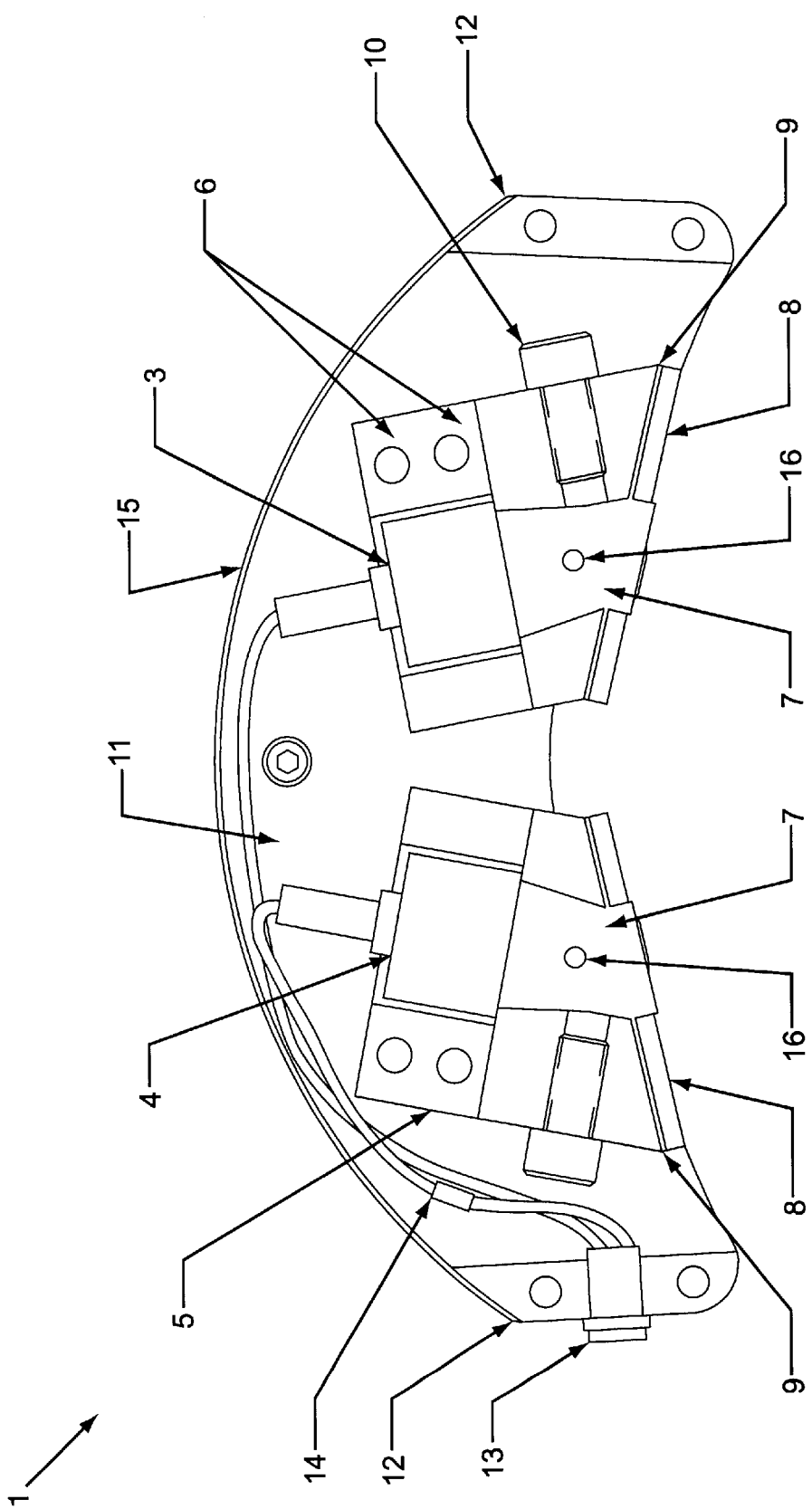
FIG. 1 is a schematic of a VAM MIC ultrasonic scanning head.

A hand-held variable angle membrane (VAM) MIC ultrasonic scanning head is described for fast and repeatable coupling of ultrasound into containers such as pipes, tanks, plates, pressure vessels, etc., for the detection of corrosion, MIC and foreign obstructions. It will be understood that the methods and apparatus herein are used for examining the inner or outer walls of essentially any type of container. As used herein, the term "container" is intended broadly to apply to any structure that can be said to encompass a given volume, or even to define a portion of a given volume. Such structures include, without limitation, pipes and other conduits, whether partly or fully open or partly or fully closed, tanks, cylinders, plates, pressure vessels, etc. In general, when specifically referring to any of these (e.g., pipes) herein, it will be appreciated that similar methods, apparatus, devices systems, etc., can be applied to any reasonably similar structural form.

The device is particularly useful for detection using leaky guided wave ultrasonic (LGWU) or guided wrap wave ultrasonic (GWWU) methods. Overall systems and methods for performing LGWU or GWWU can be found in "NON-INVASIVE DETECTION OF CORROSION, MIC, AND FOREIGN OBJECTS IN FLUID-FILLED CONTAINERS USING LEAKY GUIDED ULTRASONIC WAVES" U.S. Ser. No. 09/613,704, filed Jul. 11, 2000 by Gorman et al., and "NONINVASIVE DETECTION OF CORROSION, MIC AND FOREIGN OBJECTS IN CONTANIERS USING GUIDED ULTRASONIC WAVES," U.S. Ser. No. 09/613,705, filed Jul. 11, 2000. These systems and methods can be adapted to the present invention by the inclusion of the hand-held VAM scanning head described herein for the excitation and detection of ultrasonic waves in pipes and other containers.

Briefly, in LGWU methods, the pipe or other container is typically filled with fluid for the detection of obstructions and corrosion in the container. A transmitting transducer excites a guided wave, and part of the wave's energy leaks into the fluid. The leaky wave travels through the fluid, reflects off the pipe inner wall and enters a receiving transducer. Since the leakage field interacts directly with the fluid and inner pipe wall, the leaky guided wave ultrasonic method is able reliably to detect corrosion and MIC on the pipe inner wall, and any foreign objects inside the fluid. GWWU methods utilize an interaction of direct and wrap waves with internal corrosion and obstructions in the pipes or other containers for detection of corrosion and obstructions. Further details for LGWU and GWWU methods and appropriate systems are found in the references noted above.

Accordingly, the present device includes VAM scanning head devices. The devices comprise, e.g., a frame, a transmitting transducer rotatably mounted to the frame, and a receiving transducer rotatably mounted to the frame.

The "frame," or "external housing" is generally rigid (i.e., is typically made from a metal such as iron, steel, aluminum, copper or an alloy, but alternately can be made from a rigid polymer or other material laminate). The frame can be fabricated in a single piece, but is more conveniently fabricated to include removable portions to permit access to the transducers mounted on the frame. Thus, the frame can be a single piece, or can be made from more than one frame components which are joined together (e.g., with screws, nuts and bolts, rivets, welds, combinations thereof, or the like).

Figure 2:
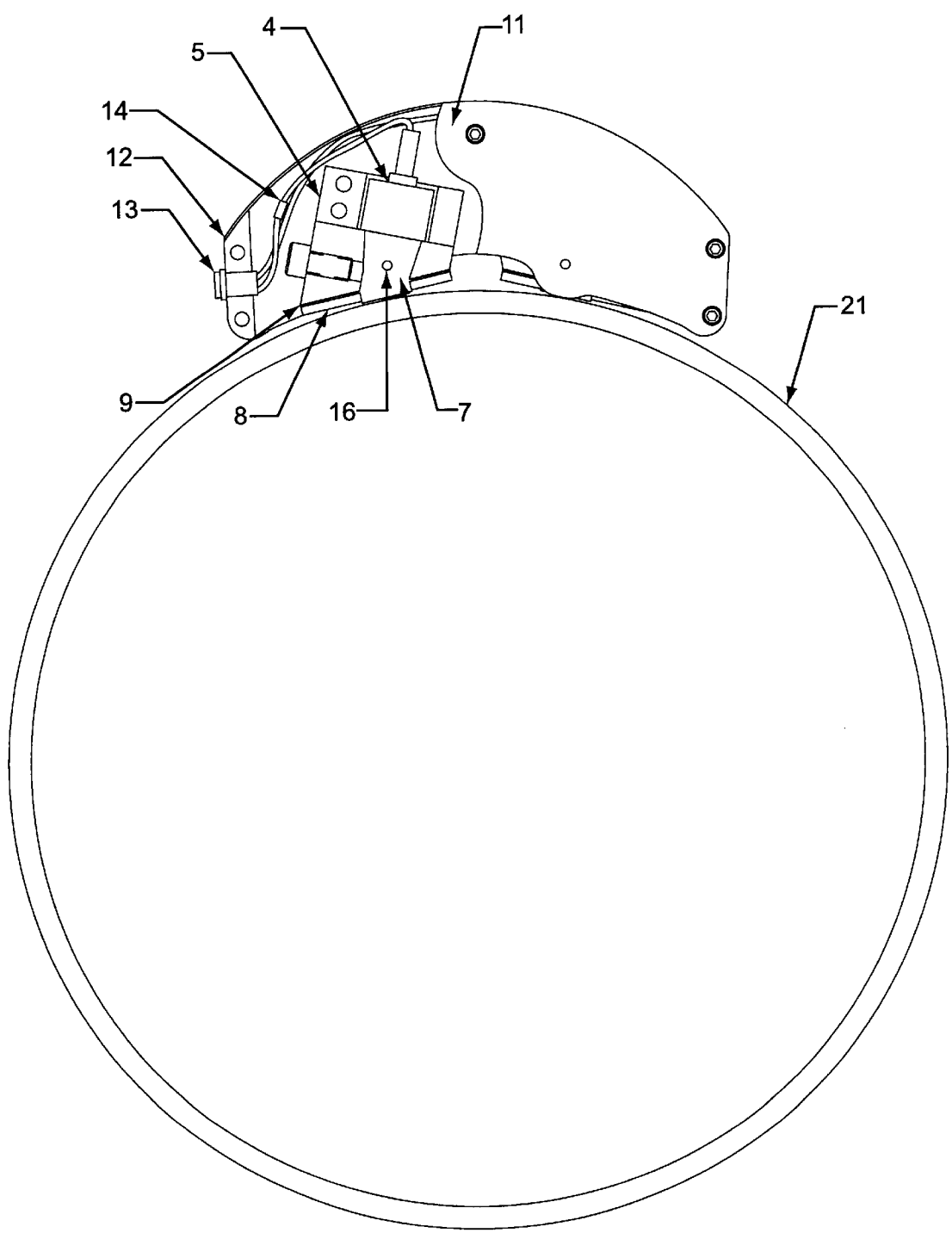
FIG. 2 is a schematic of a VAM MIC ultrasonic scanning head in use for pipe/container testing.

In one typical embodiment described in more detail in FIG. 1 and FIG. 2, the frame comprises a first side plate, a first end plate abutting the first side plate, a second side plate abutting the first end plate and a second end plate abutting the first and second side plates. Similarly, the frame optionally comprises a protective cover abutting the first side plate, the second side plate, the first end plate and the second end plate, which cover protects the transducers mounted to the frame.

The transmitting and receiving transducers typically include a transmitting or receiving plate that is coupled to, e.g., a piezoelectric element that converts electrical signals into motion of the plate (for the transmitting transducer), or motion of the plate into electrical signals (for the receiving transducer). The transducing plates are typically fluidly coupled to a membrane which is coupled to a container during operation of the device. In this embodiment, the transducers can be considered to include the piezoelectric elements, the plate, fluid couplant (e.g., contained in a housing) and the membrane, or, alternately, the transducers can be considered to simply constitute the piezoelectric and plate components, with the housing, fluid couplant and membrane being considered separate elements. Thus, optional elements of the receiving or transmitting transducer include one or more fluid filled transducer housings which couple ultrasound from a transducing face of the receiving or transmitting transducer to a rubber membrane. The flexible rubber-like membrane which couples ultrasound from the device into one or more containers over a more than one surface conditions or more than one diameters of the containers can be considered part of the transducer, or separate from the transducer.

During operation of the device, the transmitting and receiving transducers are rotated into position to conform to one or more pipe or other container diameters. Typically, the transmitting and receiving transducers are mounted to the frame on a pivot pin or other rotatable element (e.g., a ball and socket, a bearing race, or the like). The transmitting and receiving transducers typically comprise one or more means for being locked into place, such as spring loaded positioning pins, which contact detents in the frame when engaged. Other suitable arrangements include, without limitation, screws and backer plates, clips, magnetic fasteners, through pins which extend from the transducer or a transducer housing into the frame, ratcheting mechanisms, and the like. In addition to simple rotation, the receiving transducer or the transmitting transducer are optionally articulated to produce different angles between the receiving transducer or the transmitting transducer and a container, thereby providing more than one mode of ultrasound propagation by the device.

Thus, the frame can also include detents, holes, clip holders, magnetic fastener mounts or other features for locking the transducers into one or more positions. Typically, the frame will include, and/or have mounted, positioning markings that indicate proper positioning of the transducers for various pipe or other container diameters. For example, the frame can include removable and interchangeable side plates, comprising one or more detents and one or more position makings to provide controlled positioning of the transmitting transducer and the receiving transducer and to indicate one or more settings for a selected range of containers to be tested by the device.

In one embodiment, the transmitting or receiving transducer are fluidly coupled to a chamber having a fill port and a fill plug, wherein, during operation of the device, the chamber is filled with a couplant fluid which is delivered to the chamber through the fill port. The couplant fluid is retained in the chamber with the fill plug. It will be appreciated that the fill port and fill plug can take several forms, including a hole or tube into the chamber which is capped with a plug, screw, cap, stopper, cork, valve, stopcock, or the like. The couplant can be almost any fluid, e.g., water, oil, hydraulic fluid, etc. (the choice of fluid can be made to avoid damage to the transducer and membrane), or can be a gel or other fluidly deformable material.

As noted, the VAM scanning head device typically comprises one or more membranes in contact with the couplant fluid, which fluidly couples the one or more membranes and the transmitting or receiving transducer, or transmitting or receiving transducer plates. Typically, the transmitting and receiving transducers each comprise or are fluidly coupled to one or more membranes, which are shaped to extend beyond a base of the frame, permitting the membranes to deform in a fluid-like manner to a surface of one or more container during operation of the device.

The membrane can be fabricated from rubber or any rubber-like material, including natural or synthetic rubber, a natural or synthetic polymer, or the like. The material should be deformable to permit coupling to walls of a container, and generally able to hold the couplant of interest. Thus, membrane materials are selected for deformability, stability under the conditions that the device is used under and the like.

During operation of the device the membrane, contacts a container, or a fluid layer on the outer surface of a container (although not generally required, fluid on the outer surface of the container can enhance ultrasonic coupling of the membrane and the container).

As noted, the transmitting or receiving transducer typically comprises a piezoelectrically activated transducing face, which face excites or is excited by fluid in a chamber of the transducer. However, non-piezoelectrically driven excitation or detection methods, such as an optically coupled detector or optically driven excitation mechanism can be substituted. For example, instead of a piezoelectric transducer, the transducer can convert plate movement into an electrical signal by optically monitoring transducer plate movement, or by use of laser detection devices.

Typically, the transducing face of the receiving transducer is electrically coupled to one or more computer which records a signal from the receiving transducer. For example, in one embodiment, the transducer or the computer digitizes an analog signal from the receiving transducer plate (i.e., plate movement or an analog electrical signal corresponding to the plate movement) into a digital signal. Similarly, the transmitting transducer can be electrically coupled to one or more computer which controls a transmitting transducing face of the transducer.

The transmitting or receiving transducer is optionally coupled (e.g., electrically, by IR, or by other common computer peripheral coupling methods) to one or more computer comprising software with one or more instruction set for generation or analysis of ultrasonic waves, including, e.g., leaky guided wave or guided wrap wave ultrasound methods.

Details regarding such software are found in the references noted above. In brief, the software controls the transmission and reception of the ultrasonic pulse, performs specific analyses to evaluate and categorize the container condition, and displays both raw signals and analysis results in a user friendly format. To measure properly, the type of container is input into a database which can be added to as necessary or desired. This database includes, e.g., the material, schedule and diameter of the container, etc.

Generally, data obtained (and, optionally, recorded) by the device and/or a coupled computer system, is typically processed, e.g., by digitizing data and storing ultrasonic wave information or other data and analyzing the data in a computer system. A variety of commercially available peripheral equipment and software is available for digitizing, storing and analyzing a signal or image. A computer is commonly used to transform signals from the device into container wall thickness information, presence of MIC, fluids, slimy fluids or the like. Software for determining such information are available or can be constructed by one of skill using a standard programming language such as Visualbasic, Fortran, Basic, Java, or the like, or can even be programmed into simple end-user applications such as excel or Access. Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive, and other elements. Inputting devices, such as a keyboard, mouse or touch screen optionally provide for input from a user to control the transmitting transducer or to assess information from the receiving transducer.

A feature of the software which controls/analyzes data from the device optionally provides for device or system calibration. For example, by selecting a "CAL" button on a control screen, a standard waveform for a new container of that material, schedule and diameter is displayed just above that of the container being tested. This provides the operator with a useful visual comparison to supplement any analysis algorithms. This becomes particularly helpful when the container schedule changes unexpectedly, as it often does, e.g., in older systems that have undergone repairs.

The following provides a basic flowchart/outline of the operations performed by an exemplar software module:
1. Select pipe or other container parameters (schedule and diameter).
2. Select measurement, e.g., thickness or obstruction.
3. Select calibration waveform (this is optional)
4. Acquire data: pulse shape and frequency are downloaded from an internal database; the pulse is sent out of the pulser board in the computer. The pulse is amplified and excites the transmitting transducer. The pulse is detected by the receiving transducer, fed to receiver electronics, and then fed into an analog to digital converter and stored in digital electronic format in the computer.
5. Analyze data: received waveform(s) is/are compared with calibration signal(s) and, e.g., in LGWU applications, direct waves are compared to energies of multiple leaky or direct waves as well as the direct wave. For GWWU applications, the received waveform(s) is/are compared with calibration signal(s), with both regular and wrap waves being tested.

6. Raw data is displayed as received signal(s) and analysis result(s).
7. Stored calibration pulse waveform for good container(s) are displayed.

The computer and the VAM scanning device can be operably coupled in a variety of ways, including electrical coupling, IR, laser or other optical coupling methods, storage of data by the VAM device to magnetic media, which is later inserted into the computer, or the like. For example, in one convenient operation, the VAM scanning device can include one or more quick connect/disconnect electrical connectors mounted on the frame, which connectors are electrically coupled to the receiving transducer, the transmitting transducer, or to both the receiving transducer and the transmitting transducer. Similarly, an IR port and/or signal emitter can be mounted on the frame, eliminating the need for a direct electrical coupling altogether.

As mentioned, the VAM scanning head device is optionally configured to be hand-held during operation. That is, the device is of an appropriate size and physical conformation to be grasped in one or both hands to contact the device to the pipe or other container to be monitored, during operation of the device. For the device to be hand-held it is also appropriate for the device to be properly shielded to prevent electrical hazard to the user.

As noted throughout, the present invention includes both a new device and new methods, e.g., of using the device. For example, in one aspect, the invention provides methods for detecting container features, or fluids or other materials inside a fluid filled container. The method includes contacting the container with a hand held VAM scanning device, which comprises a rotatably mounted receiving transducer and a rotatably mounted transmitting transducer, exciting the transmitting transducer to produce one or more ultrasonic waves in the container, and detecting the one or more ultrasonic waves by detecting a signal from the receiving transducer. As noted above, the receiving transducer and/or the transmitting transducer are typically rotated to conform to the container. Also as noted, the methods typically include exciting the transmitting transducer, e.g., by activating a piezoelectrically or otherwise controlled transducing plate in the transmitting transducer. Similarly, the transmitting transducer is controlled through a computer or analog signal generation device electrically coupled to the transmitting transducer. Detecting the ultrasonic waves can include e.g., LGWU or GWWU detection. The methods optionally include digitizing a detected ultrasonic wave and storing information corresponding to the digitized wave in a database.

In one example configuration, a VAM MIC ultrasonic scanning head of the invention includes, e.g., the following components, e.g., as shown in FIG. 1 and FIG. 2 (one of skill will recognize that certain components are optional and that other configurations, e.g., in accordance with the foregoing and the following will be equally preferred):

1—Head
3—Transmitting piezoelectric ultrasonic transducer
4—Receiving piezoelectric ultrasonic transducer
5—Transducer housing
6—Spring loaded transducer positioning pins
7—Coupling fluid
8—Membrane attachment plate
9—Thin rubber membrane
10—Fill plugs
11—Side plates
12—End Plates
13—Electrical connectors
14—Line driver
15—Cover
16—Pivot pins FIG. 1 shows a schematic of VAM MIC ultrasonic scanning head 1. Head 1 comprises transmitting transducer 3, receiving transducer 4, transducer housings 5, spring loaded transducer positioning pins 6, coupling fluid 7, membrane attachment plate 8, thin rubber or other polymer membrane 9, fill plugs 10, side plates 11, end plates 12, electrical connectors 13, line driver 14, cover 15 and pivot pins 16. Transducers 3 and 4, are mounted into transducer housing 5 and sealed with either a sealant or a rubber O-ring.

Thin rubber membrane 9 is attached to transducer housing 5 with membrane attachment plate 8 and associated screws. Coupling fluid 7 is put into the transducer housing cavity between the transducers 3 and 4 and thin rubber membrane 9 through the fill holes, and then sealed with fill plugs 10. Transducer housings 5 are mounted between the side plates 11 on pivot pins 16, which allow transducer housings 5 to rotate. Positioning detents machined into the side plates to receive the spring loaded positioning pins 6 control transducer positioning. Locator lines are machined into the side plates so that the transducer angle can be easily adjusted for various pipe diameters.

Side plates 11 are attached to the end plates 12 to form a rigid frame to hold the transducer housings 5. Transmitting transducer 3 and receiving transducer 4 are attached to electrical connectors 13. Receiving transducer output is amplified with line driver 14. Cover 15 is used to protect transducers 3 and 4 and connectors 13.

The VAM MIC scanning head couples ultrasound out of transmitting transducer 3 and into the pipe to become guided waves propagating away from the transducer along the pipe wall. At the same time, it couples ultrasound into receiving transducer 4.

The VAM MIC scanning head is placed on pipe or other container 21 as shown in FIG. 2. For clarity, the view shows a partial cutaway of side plate 11. Rubber membrane 9 is coupled to pipe 21 using a small amount of a suitable ultrasound couplant, such as water or ultrasonic gel. A high voltage signal is input into the (e.g., piezoelectric) transmitting transducer through the electrical connections. The electrical signal is converted to ultrasound by the transducer. The ultrasound is coupled from the transducer to the rubber membrane through the fluid contained in the transducer housing. The rubber membrane deforms to match the curvature of the pipe outer wall, and couples the ultrasound into the pipe wall. The signal travels along the pipe wall as shown in FIG. 2, and is collected by the receiving transducer. The wave travels through the rubber membrane, through the coupling fluid and into the receiving transducer. The output signal from the receiving transducer is amplified using a line driver and the signal is sent to a processing unit over an electrical cable.

The VAM MIC scanning head can be adjusted to accommodate various sizes and thicknesses of pipe diameters. By rotating the transducer housings to preset locations determined by the detents, the correct transducer angle for GWWU and LGWU generation is obtained. The rubber membrane deforms to accommodate the various pipe diameters and the fluid contained in the transducer housing couples the ultrasound from the transducer to the rubber membrane. The rubber membrane is coupled to the outer wall of the pipe using a small amount of suitable ultrasonic couplant.

Various types of fluids can be used in the transducer housing. These may consist of water, ethylene glycol, oil or other suitable coupling agents for the range of temperatures at which the inspection is to be performed. The membrane is manufactured from any suitable material that allows ultrasound transfer, such as latex, rubber, neoprene, etc. The rubber thickness is typically substantially less than the wavelength of the sound propagating in the coupling fluid.

While the above description contains many specific examples, these should not be construed as limitations on the scope of the invention, but rather as illustrative embodiments thereof. Many other variations are possible and will be apparent to one of skill upon review of this disclosure. For example, different side plates can be manufactured for various ranges of pipe diameters and wall thicknesses. The transducers can also be oriented to propagate the wave between the transducers to scan smaller areas. Another example is to modify the scanning head to inspect containers of non-circular shapes, such as cubes and cones. The VAM ultrasonic scanning head can be used on pipes, tanks, plates, pressure vessels, etc.

The foregoing description of embodiments of the invention has been presented for purposes of illustration and description. The description is not intended to be exhaustive or to limit the invention to the precise form disclosed, and many modifications and variations are possible in light of the above teaching. Such modifications and variations, which may be apparent to a person skilled in the art, are within the scope of this invention. All patent applications, patents, patent documents and other publications cited herein are incorporated by reference in their entirety for all purposes to the same extent as if each item were so individually denoted.

What is claimed is:

1. A VAM scanning head device, comprising:
   a frame;
   a transmitting transducer housing rotatably mounted to the frame, wherein the transmitting transducer housing houses a transmitting transducer; and,
   a separate receiving transducer housing rotatably mounted to the frame, wherein the receiving transducer housing houses a receiving transducer.

2. The VAM scanning head device of claim 1, wherein the frame is rigid.

3. A VAM scanning head device, comprising:
   a frame;
   a transmitting transducer rotatably mounted to the frame; and
   a receiving transducer rotatably mounted to the frame, wherein the frame comprises a first side plate, a first end plate abutting the first side plate, a second side plate abutting the first end plate and a second end plate abutting the first and second side plates.

4. The VAM scanning head device of claim 3, the frame further comprising a protective cover abutting the first side plate, the second side plate, the first end plate and the second end plate.

5. The VAM scanning head device of claim 4, wherein the transmitting and receiving transducers a re fluidly coupled to a membrane which is coupled to a container during operation of the device.

6. The VAM scanning head device of claim 1, wherein, during operation of the device, the transmitting and receiving transducer housings are rotatable into position to conform to one or more pipe or other container diameters.

7. The VAM scanning head device of claim 1, wherein the transmitting and receiving transducer housings are mounted to the frame on a pivot pin.

8. The VAM scanning head device of claim 1, the transmitting or receiving transducer housings comprising one or more spring loaded positioning pins, which pins contact detents in the frame when engaged, thereby locking the transmitting or receiving transducer into position.

9. The VAM scanning head device of claim 1, the frame comprising removable and interchangeable side plates, the side plates comprising one or more detents and one or more position markings to provide controlled positioning of the transmitting transducer and the receiving transducer and to indicate one or more settings for a selected range of containers to be tested by the device.

10. The VAM scanning head device of claim 1, wherein the receiving transducer or the transmitting transducer housings are rotated with respect to one another to produce different angles between the receiving transducer or the transmitting transducer and a container, thereby providing more than one mode of ultrasound propagation by the device.

11. The VAM scanning head device of claim 1, wherein the transmitting or receiving transducer housings are filled with a couplant fluid.

12. The VAM scanning head device of claim 11, comprising one or more membranes in contact with the couplant fluid, wherein the couplant fluid fluidly couples the one or more membranes to the transmitting or receiving transducer.

13. The VAM scanning head device of claim 12, wherein the membrane, during operation of the device, contacts a container, or which contacts a fluid layer on an outer surface of a container.

14. The VAM scanning head device of claim 1, the transmitting and receiving transducer housings each mounting one or more membranes, which membranes are shaped to extend beyond the transmitting or receiving transducer housings, permitting the membranes to deform in a fluid-like manner to a surface of one or more container during operation of the device.

15. The VAM scanning head device of claim 1, the transmitting or receiving transducer comprising or being fluidly coupled to a membrane, which membrane, during operation of the device, contacts a container or which contacts a fluid layer on the outer surface of a container.

16. The VAM scanning head device of claim 1, the receiving or transmitting transducer comprising one or more fluid filled transducer housings wherein fluid in the fluid filled transducer housings couples ultrasound from a piezoelectric transducing face of the receiving or transmitting transducer to a rubber membrane.

17. The VAM scanning head device of claim 1, comprising a flexible rubber-like membrane which couples ultrasound from the device into one or more containers over more than one diameters of the containers.

18. The VAM scanning head device of claim 1, the transmitting or receiving transducer comprising a piezoelectric transducing face, which piezoelectric transducing face excites or is excited by fluid in a chamber of the transducer.

19. The VAM scanning head device of claim 18, wherein the piezoelectric transducing face of the receiving transducer is electrically coupled to one or more computers which digitizes an analog signal from the receiving transducer.

20. The VAM scanning head device of claim 18, wherein the piezoelectric element of the transmitting transducer is electrically coupled to one or more computers which controls the piezoelectric transducing face.

21. The VAM scanning device of claim 18, wherein the transmitting or receiving transducer is electrically coupled to one or more computers comprising software with one or more instruction sets for generation or analysis of leaky guided wave or guided wrap wave ultrasound.

22. The VAM scanning device of claim 1, further comprising one or more quick connect/disconnect electrical connectors mounted on the frame, which connectors are electrically coupled to the receiving transducer, the transmitting transducer, or to both the receiving transducer and the transmitting transducer.

23. The VAM scanning head device of claim 1, wherein the device is hand-held during operation.

24. A method for detecting container features, or fluids or other materials inside a fluid filled container, the method comprising:

contacting the container with a hand held VAM scanning device, which scanning device comprises a rotatably mounted receiving transducer housing that houses a receiving transducer and a rotatably mounted transmitting transducer housing that houses a transmitting transducer;

exciting the transmitting transducer to produce one or more ultrasonic waves in the container; and, detecting the one or more ultrasonic waves by detecting a signal from the receiving transducer.

25. The method of claim 24, comprising rotating the receiving transducer or the transmitting transducer to conform to the container.

26. The method of claim 24, wherein exciting the transmitting transducer comprises activating a piezoelectrically controlled transducing plate in the transmitting transducer.

27. The method of claim 24, wherein the transmitting transducer is controlled through a computer or analog signal generation device electrically coupled to the transmitting transducer.

28. The method of claim 24, wherein detecting the ultrasonic waves comprises LGWU or GWWU detection.

29. The method of claim 24, wherein the detection comprises digitizing a detected ultrasonic wave and storing information corresponding to the digitized wave in a database.

* * * * *